(12) United States Patent
Matsumura et al.

(10) Patent No.: US 6,267,723 B1
(45) Date of Patent: Jul. 31, 2001

(54) MEDICAL TELEMETERY SYSTEM, AND A SENSOR DEVICE AND A RECEIVER FOR THE SAME

(75) Inventors: Fumiyuki Matsumura; Tetsushi Sekiguchi; Hiroshi Sakata; Hidehiro Hosaka; Kohei Ono, all of Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 09/260,612

(22) Filed: Mar. 2, 1999

(30) Foreign Application Priority Data

Mar. 2, 1998 (JP) .................................................. 10-049314

(51) Int. Cl.[7] ...................................................... A61B 5/00
(52) U.S. Cl. ........................................... 600/300; 128/903
(58) Field of Search ..................................... 600/300, 508, 600/520, 522, 523; 607/60; 128/703

(56) References Cited

U.S. PATENT DOCUMENTS

| | | | |
|---|---|---|---|
| 4,121,573 | * 10/1978 | Corovella et al. | ................... 128/903 |
| 4,319,241 | * 3/1982 | Mount | .................................. 128/903 |
| 4,625,733 | * 12/1986 | Saynajakangas | ..................... 128/903 |
| 5,131,399 | * 7/1992 | Sciarra | .................................. 128/903 |

* cited by examiner

Primary Examiner—George R. Evanisko
(74) Attorney, Agent, or Firm—Sughrue, Mion, Zinn, Macpeak & Seas, PLLC

(57) ABSTRACT

A sensor device a sensor unit which detects a biomedical signal, and a transmitter which converts the biomedical signal into a radio signal and then transmits the radio signal. The transmitter has an electrode detachment detection unit 12 which detects electrode detachment on the basis of an output of the sensor unit, and transmits an electrode detachment signal indicative of the detachment. In a receiver, the biomedical signal transmitted from the transmitter is received, the signal is attenuated by an attenuation unit, and the attenuated signal is supplied to a wired sensor input portion of another device through a switch and a connection unit. In the receiver, when the electrode detachment signal is detected from the signal transmitted from the transmitter, the switch is turned off.

15 Claims, 14 Drawing Sheets

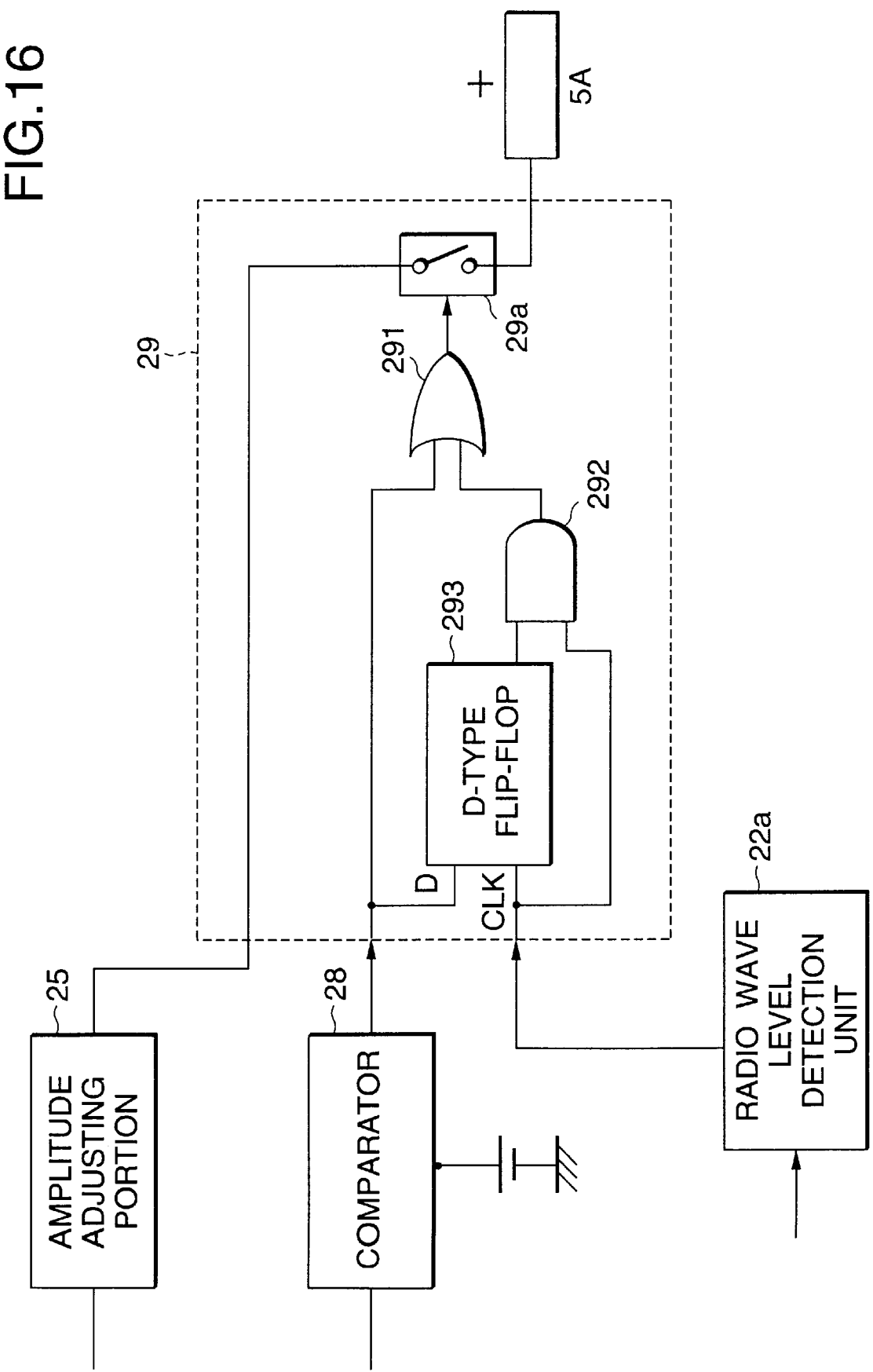

MEDICAL TELEMETERY SYSTEM, AND A SENSOR DEVICE AND A RECEIVER FOR THE SAME

BACKGROUND OF INVENTION

1. Field of the Invention

The present invention relates to a medical telemetry system in which an electrode is attached to a patient to monitor the condition of the patient.

2. Related Art

The condition of a patient is monitored in a route from an emergency rescue scene to an emergency rescue facility or the like to which the patient is to be transported. In such a case, conventionally, a sensor and an input cord must be replaced with other ones each time when a different medical apparatus is used in various situations as shown in FIG. 9.

When a sensor and an input cord are replaced with other ones in various situations, however, a burden is imposed on a patient in each replacement. In an emergency rescue scene where prompt treatment is necessary, the time required for the replacement is a problem.

SUMMARY OF INVENTION

The invention has been conducted in view of the disadvantages of the prior art. It is an object of the invention to, even when an apparatus for processing a signal from a sensor is replaced with a new apparatus, enable the signal to be rapidly supplied to the new apparatus by a simple operation and without imposing a burden on a patient and medical staff.

According to an aspect of the present invention, there is provided a medical telemetry system comprising:

a sensor device including:

an electrode to be attached to a living body;

first detecting means for detecting electrode detachment on the basis of a signal obtained from said electrode, and for outputting an electrode detachment signal indicative of the electrode detachment;

transmitting means for transmitting the electrode detachment signal from said first detecting means and a biomedical signal from said electrode, in the form of a radio signal;

a receiver including:

receiving means for receiving the radio transmitted from said sensor device;

amplitude adjusting means for attenuating or amplifying the biomedical signal obtained from an output signal of said receiving means to adjust an amplitude of the biomedical signal;

connecting means for supplying an output signal of said amplitude adjusting means to a biomedical signal input portion of another device;

second detecting means for detecting the electrode detachment signal from the output signal of said receiving means; and means, connected between said amplitude adjusting means and said connecting means, for interrupting connection between said amplitude adjusting means and said connecting means or for increasing an impedance of the connection when said second detecting means detects the electrode detachment signal.

In the system, a biomedical signal which is transmitted in the form of a radio signal from the sensor device is received by the receiver. After being attenuated or being amplified, the signal is supplied to a biomedical singal input portion of another device which is connected to the receiver. The other device processes the signal. Since the signal is converted to the same level as a signal supplied from a biomedical electrode through a wire, the result of the process is identical with that for the signal which is directly supplied from a biomedical electrode. Even when the receiver is disconnected from the other device and then connected to a further device while the sensor device remains attached to the living body, therefore, the signal is processed by the further device in the same manner as a signal supplied from a biomedical electrode through a wire.

When the electrode of the sensor device is detached from the living body, the first detecting means detects the electrode detachment, and the transmitting means transmits the electrode detachment signal to the receiving means. The second detecting means of the receiver detects the signal. In response to the detection, the connection between the attenuating means and the connecting means is interrupted or an impedance of the connection is increased. In the other device which is connected to the receiver through the connecting means, the input potential of the biomedical signal input portion is in a floating state. As seen from the other device, this state is strictly identical with that obtained in the case where, when a signal supplied from the biomedical electrode through a wire is being processed, the biomedical electrode is detached.

Usually, a device which processes a signal supplied from a biomedical electrode through a wire has functions of detecting electrode detachment and conducting a process according to the detected detachment. The system of the invention corresponds to such a device. Although the signal transmitted from the electrode is a radio signal, when the electrode is detached from the living body, a state where electrode detachment occurs is artificially produced in the wired sensor input portion of the other device.

According to another aspect of the present invention, there is provided a sensor device for a medical telemetry system, comprising:

an electrode which is to be attached to a living body;

first detecting means for detecting electrode detachment on the basis of a signal obtained from said electrode, and for outputting an electrode detachment signal indicative of the electrode detachment; and transmitting means for transmitting the electrode detachment signal from said first detecting means and a biomedical signal from said electrode, in the form of a radio signal.

In the thus configured sensor device, a biomedical signal is transmitted, and, when the electrode which has been attached to the living body is detached, a signal indicative of the electrode detachment is transmitted.

According to another aspect of the present invention, there is provided a receiver for a medical telemetry system, comprising:

receiving means for receiving a radio signal containing a biomedical signal and an electrode detachment signal indicative of electrode detachment;

amplitude adjusting means for attenuating or amplifying the biomedical signal obtained from an output signal of said receiving means to adjust an amplitude of the biomedical signal;

connecting means for supplying an output signal of said amplitude adjusting means to a biomedical signal input portion of another device;

second detecting means for detecting the electrode detachment signal from the output signal of said receiving means; and means, connected between said amplitude adjusting means and said connecting means, for interrupting connection between said amplitude adjusting means and said connecting means, or for increasing an impedance of the connection when said second detecting means detects the electrode detachment signal.

In the thus configured receiver, a biomedical signal in the received signal is attenuated or amplified, and then supplied to the other device connected to the receiver. The signal has the same level as a signal supplied from a biomedical electrode through a wire. In the receiver, when the electrode detachment signal is detected, the connection between the amplitude adjusting means and the connecting means is interrupted in response to the detection. Therefore, in the other device which is connected to the receiver, the input potential of the biomedical signal input portion is in a floating state.

BRIEF DESCRIPTION OF THE DRAWINGS

FIG. 16 is a diagram showing the configuration of the receiver of the present invention.

DETAILED DESCRIPTION OF PREFERRED EMBODIMENTS

Figure 2:
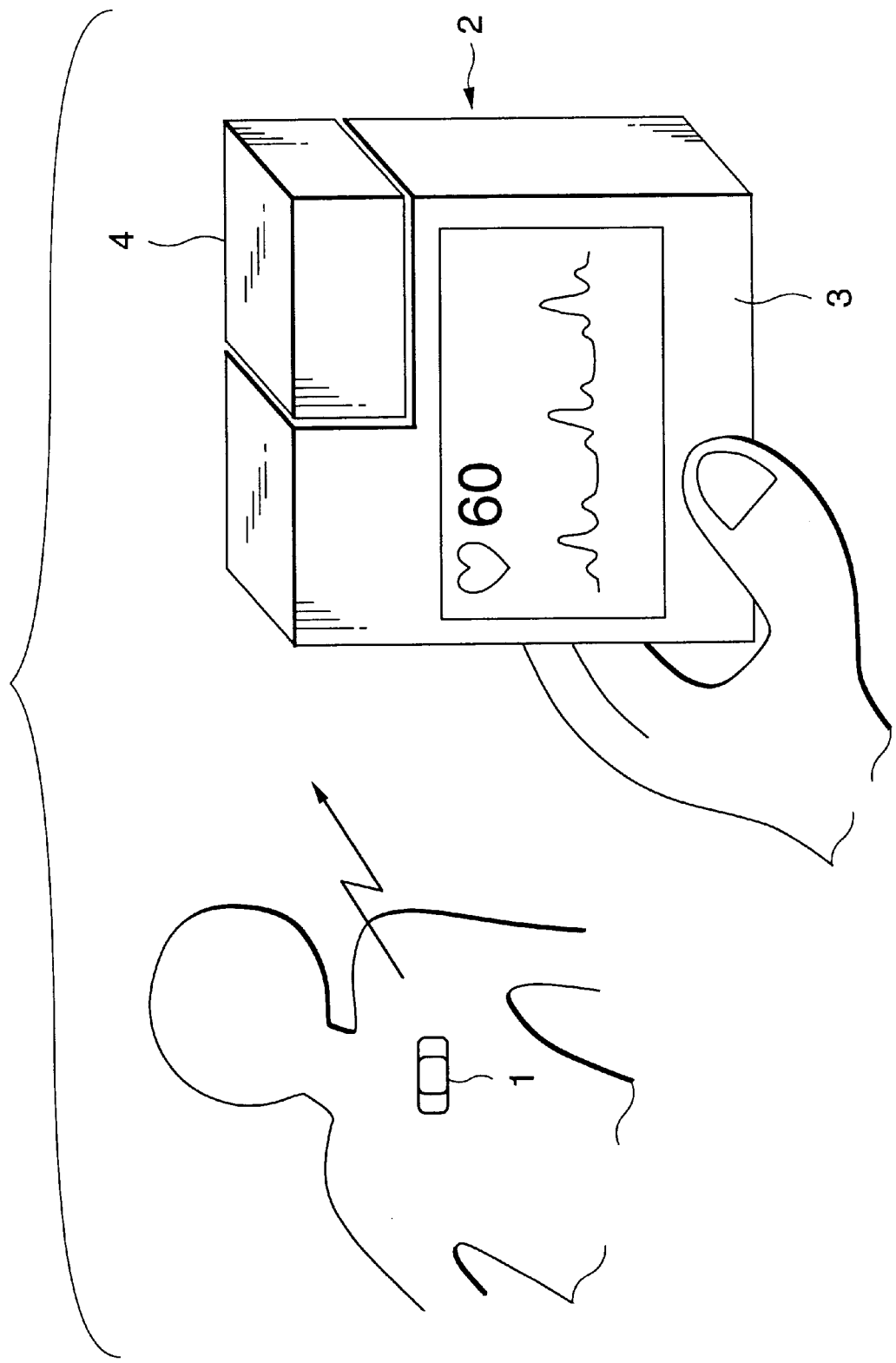
FIG. 2 is a view showing the whole configuration of the first embodiment of the invention.
Figure 3:
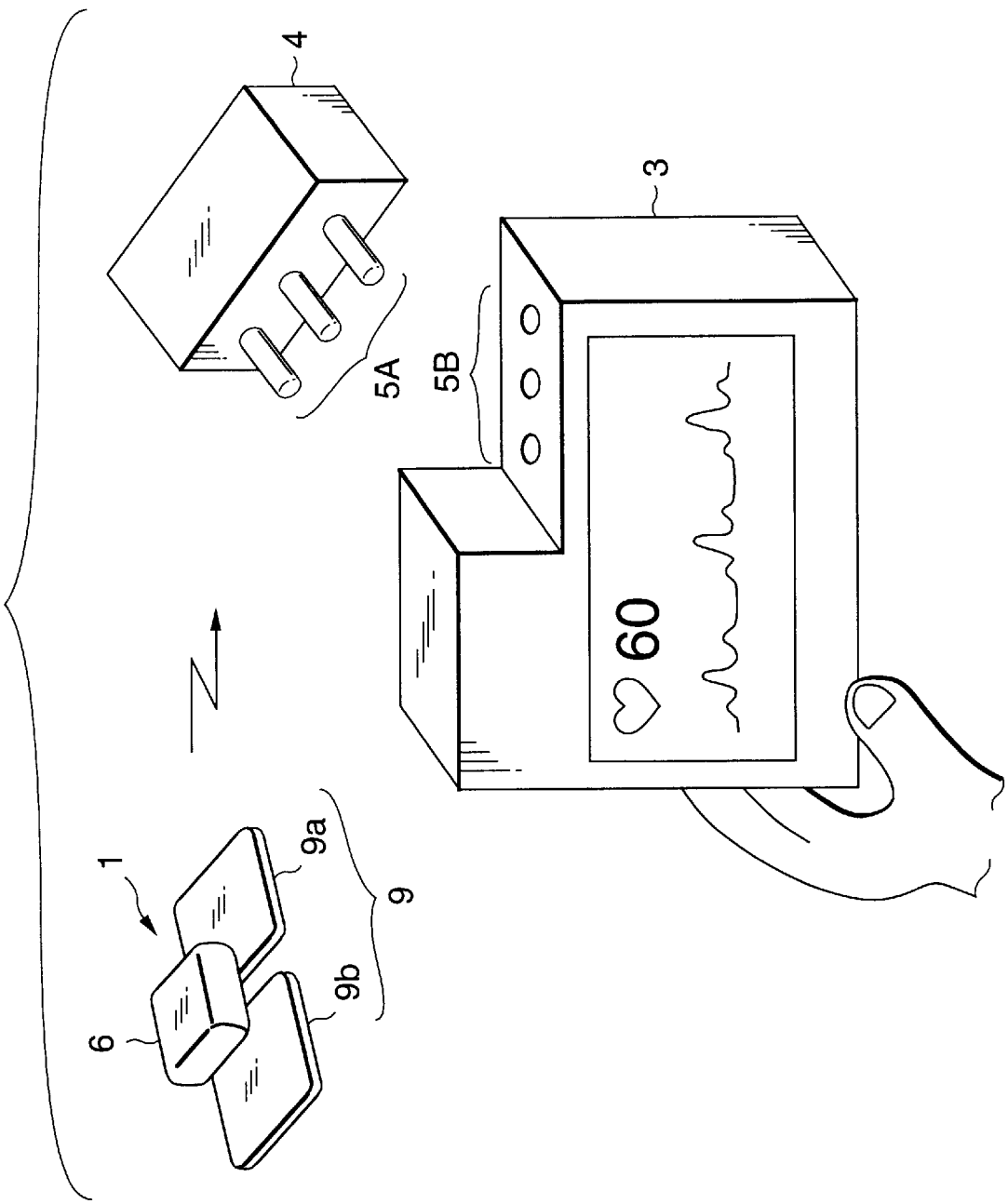
FIG. 3 is a view illustrating a method of using the system shown in FIG. 2.
Figure 4:
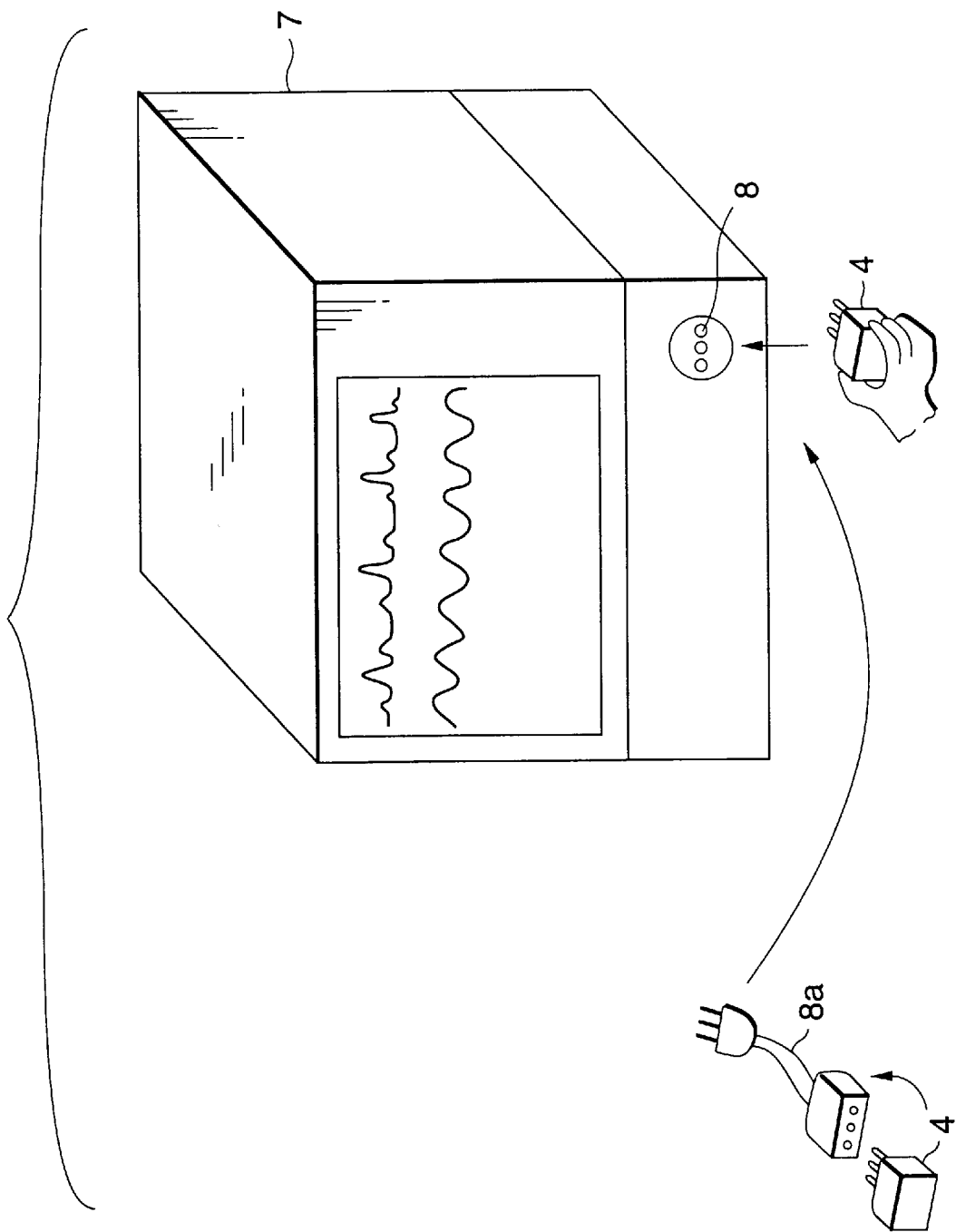
FIG. 4 is a view illustrating a case where the system shown in FIG. 2 is used with replacing the monitor device with another one.

FIG. 2 shows the whole configuration of the medical telemetry system of the invention. As shown in the figure, a sensor device 1 is attached to a patient. The sensor device 1 detects a biomedical signal, and transmits the biomedical signal in the form of a radio signal to a portable patient monitoring device 2. The portable patient monitoring device 2 consists of a display device 3 and receiver 4. As shown in FIG. 3, the receiver 4 has a connector 5A so as to be attachable and detachable from a connector 5B of the display device 3. When the connectors 5A and 5B are joined to each other, the display device 3 and the receiver 4 form a single box-like shape as shown in FIG. 2. FIG. 4 is an external view of a display device 7 which is used as a bedside monitor. The connector 5A of the receiver 4 shown in FIG. 2 is attachable and detachable also from a connector 8 of the display device 7 and serving as a biomedical signal input portion. When the connector 5A cannot be connected to some other bedside-monitor via input connector 8, and additional conversion connector may be used therebetween in detachable manner.

FIG. 3 shows also the sensor device 1 in an enlarged manner. The sensor device 1 consists of a transmitter 6 and a sensor unit 9. The sensor unit 9 consists of a pair of electrodes 9a and 9b.

Figure 1:
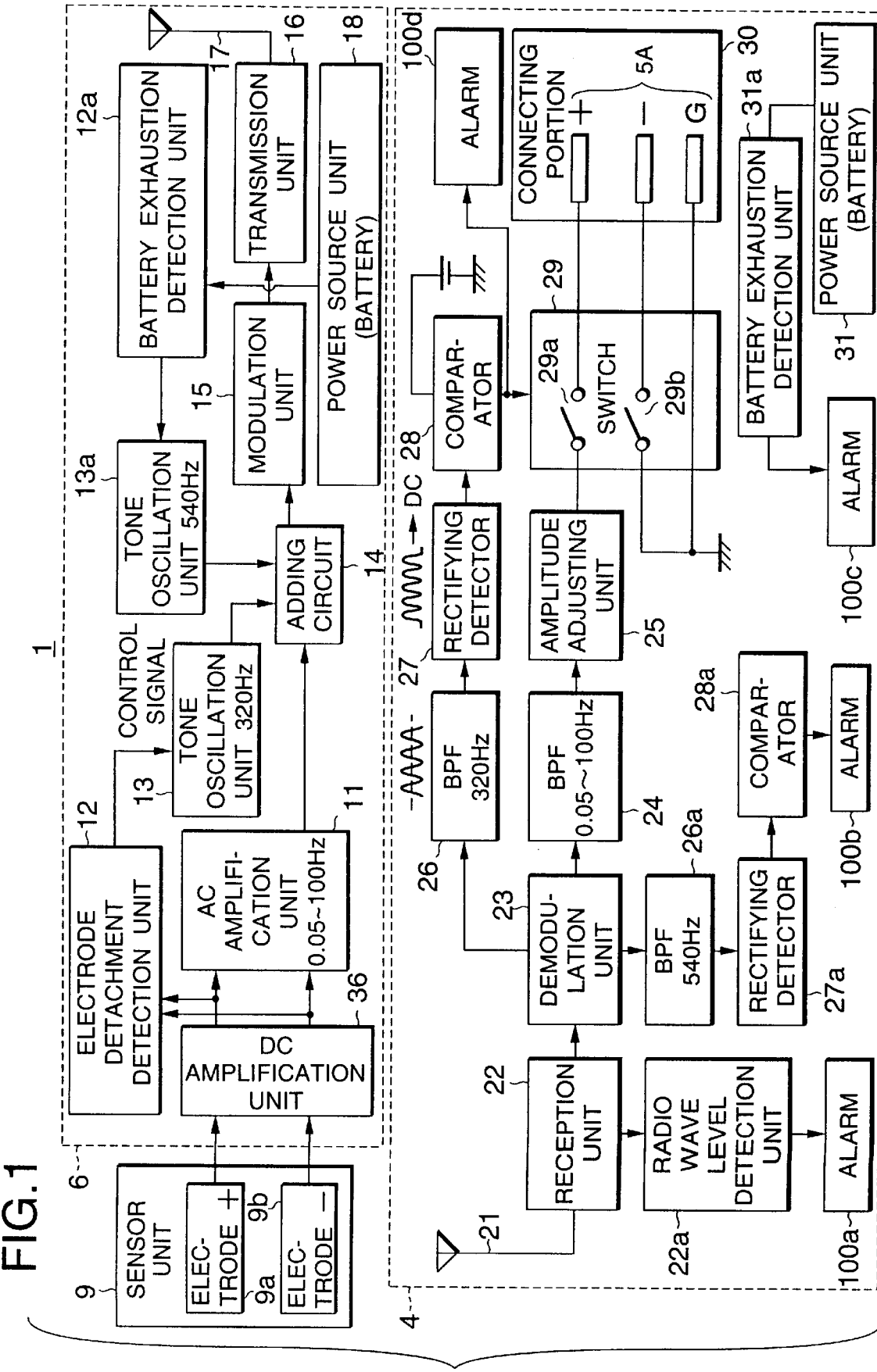
FIG. 1 is a diagram showing the internal configuration of a sensor device and a receiver of a first embodiment of the invention.

FIG. 1 shows the internal configuration of the sensor device 1 and the receiver 4. The sensor unit 9 of the sensor device 1 is configured as described above. The transmitter 6 consists of a DC amplification unit 36, and AC amplification unit 11, an electrode detachment detection unit 12, a tone oscillation unit 13, an adding circuit 14, a modulation unit 15, a transmission unit 16, an antenna 17, and a power source unit 18.

The AC amplification unit 11 is a circuit which amplifies the potential between the paired electrodes 9a and 9b of the sensor unit 9, or a signal of 0.05 to 100 Hz that can be regarded as a biomedical signal.

The electrode detachment detection unit 12 is a circuit which detects an electrode detachment state, from an output signal of the DC amplification unit 36. Specifically, the unit detects the state where one or both of the electrodes which have been attached to the subject is detached, that where the contact resistance between the subject and the electrodes is increased, and that where the polarization voltage between the subject and the electrodes is excessively raised. As disclosed in, for example, Unexamined Japanese Patent Publication Hei. 6-269417, when the output signal of the DC amplification unit 36 exceeds a preset value, a signal indicative of the above is output. Alternatively, the technique disclosed in, for example, Examined Japanese Utility Model Publication Sho. 62- 10875 may be employed. The signal indicative of electrode detachment is used as a control signal for causing the tone oscillation unit 13 so as to output a signal of a predetermined frequency for example 320 Hz. The frequency of the tone oscillation unit 13 is not limited except for frequency-band of biomedical signal.

The adding circuit 14 is a circuit which adds output signals of the AC amplification unit 11 and the tone oscillation unit 13 to each other.

The modulation unit 15 is a circuit which modulates a carrier wave signal in accordance with an output signal of the adding circuit 14, and the transmission unit 16 is a circuit which converts an output signal of the modulation unit 15 into a radio signal and transmits the radio signal through the antenna 17. The power source unit 18 is a battery which supplies a required power to the above-mentioned components.

In addition, transmitter 6 includes a battery exhaustion detection portion 12a and tone oscillation portion 13a. When the battery exhaustion detection portion 12a detects battery exhaustion of battery portion 18, a signal indicative of the battery exhaustion is output to the tone oscillation portion 13a, and the tone oscillation portion 13a outputs for example, a 540 Hz signal. Adding circuit 14 also adds this signal.

The electrode detachment detection unit 12 and the tone oscillation unit 13 constitute the first detecting means, and the AC amplification unit 11, the adding circuit 14, the modulation unit 15, the transmission unit 16, and the antenna 17 constitute the transmitting means.

Next, the receiver 4 will be described. The receiver 4 consists of: an antenna 21; a reception unit 22 which receives the radio signal through the antenna 21; a demodulation unit 23 which demodulates the signal received by the reception unit 22; a BPF (Band-Pass Filter) 24 which extracts a signal of for example, 0.05 to 100 Hz from an output signal of the demodulation unit 23; an amplitude adjusting unit 25 which attenuates or amplifies an output signal of the BPF 24; a BPF 26 which extracts a signal of for example, 320 Hz from the output signal of the demodulation unit 23; a rectifying detector 27 which rectifies and detects an output signal of the BPF 26; a comparator 28 which judges whether an output signal of the rectifying detector 27 exceeds a preset threshold; a switch 29 having a pair of switchover portions 29a and 29b which are simultaneously switched over in response to a switchover signal that is output when the comparator 28 judges that the output signal exceeds the preset threshold; a connection unit 30 which is connected to output terminals of the switchover portions 29a and 29b of the switch 29, and which is to be connected to a connection unit of another device; and a power source unit 31. The power source unit 31 is a battery which supplies a required power to the above-mentioned components.

An output signal of the amplitude adjusting unit 25 is supplied to one terminal of the switchover portion 29a of the switch 29. The connection unit 30 has the connector 5A consisting of three pins. Among the pins, a plus pin is connected to the other terminal of the switchover portion 29a of the switch 29, a minus pin is connected to one terminal of the switchover portion 29b of the switch 29, and a ground pin is connected to the other terminal of the switchover portion 29b of the switch 29. When the switchover signal of the comparator 28 is not output, the pair of switchover portions 29a and 29b of the switch 29 are normally closed. The switchover portions 29a and 29b may be composed of analog-switch using semiconductor, relay, or photoswitch. And the electrode detachment state may be reproduced by using either of switch 29a or 29b instead using both as a pair of switchover portions 29a and 29b.

As described above, the amplitude adjusting unit 25 attenuates the signal which has been demodulated by the demodulation unit 23. The attenuation or amplification is conducted so that the level of the adjusted signal is equal to that of a weak biomedical signal which is directly obtained from the biomedical electrodes.

The antenna 21, the reception unit 22, the demodulation unit 23, and the BPF 24 constitute the receiving means. The BPF 26, the rectifying detector 27, the comparator 28 and switch 29 constitute the second detecting means, the amplitude adjusting unit 25 constitutes the amplitude adjusting means, and the connection unit 30 constitutes the connecting means.

Next, the operation of the thus configured telemetry system will be described. First, the case will be described in which, under a state where a patient can freely move, an electrocardiographic signal is monitored through the display device 3 of the portable patient monitoring device 2 shown in FIG. 2, and then monitored through the display device 7 of the bedside monitor.

The connector 5B of the display device 3, and the connector 8 of the display device 7 are disposed as a connection portion (biomedical signal input portion) for obtaining a signal from the electrodes attached to the patient through a cord. Each of the display devices 3 and 7 comprises means for, based on a signal supplied through the connector 5B or 8, detecting electrode detachment, and other means such as that for, when electrode detachment is detected, issuing an alarm.

First, the sensor device 1 is attached to a patient. Specifically, the paired electrodes 9a and 9b of the sensor unit 9 are attached to the patient, and a power source switch (not shown) of the transmitter 6 is turned on. At this time, the connectors 5A and 5B are connected to each other as shown in FIG. 3, and the receiver 4 is mounted on the display device 3 so as to attain the state of FIG. 2. Also a power source switch (not shown) of the receiver 4 is turned on.

In the sensor device 1 under this state, an electrocardiographic signal obtained from the electrode 9a and 9b is amplified in the AC amplification unit 11, and then supplied to the adding circuit 14. At this time, the electrode detachment detection unit 12 does not detect electrode detachment, and hence the adding circuit 14 outputs the signal supplied from the AC amplification unit 11, as it is to the modulation unit 15. The modulation unit 15 modulates the carrier wave signal on the basis of the output signal, and supplies the modulated signal to the transmission unit 16. The transmission unit 16 transmits the modulated wave signal through the antenna 17.

On the other hand, in the receiver 4, the reception unit 22 receives the signal transmitted from the transmitter 6, through the antenna 21, and the received signal is demodulated by the demodulation unit 23. The demodulated signal is an electrocardiographic signal of 0.05 to 100 Hz. Therefore, the signal is extracted by the BPF 24, attenuated or amplified in the amplitude adjusting unit 25, and then supplied to the connection unit 30 through the switch 29. The display device 3 performs a display based on the signal. Since the signal extracted by the BPF 24 is attenuated or amplified in the amplitude adjusting unit 25, the display device 3 receives a signal of the same level as a signal level which is obtained in the case where a sensor is directly connected to the display device through a cord.

When one or both of the electrodes 9a and 9b of the sensor device 1 is detached from the patient, the electrode detachment detection unit 12 of the transmitter 6 detects the detachment state, and transmits the control signal to the tone oscillation unit 13, thereby causing the tone oscillation unit 13 to output a signal of 320 Hz. As a result, the adding circuit 14 adds the signal of 320 Hz. As a result, the adding circuit 14 adds the signal of 320 Hz output form the tone oscillation unit 13, to the signal supplied from the AC amplification unit 11. The modulation unit 15 modulates the carrier wave signal on the basis of the signal obtained as a result of the addition, and supplies the modulated signal to the transmission unit 16. The transmission unit 16 transmits the modulated wave signal through the antenna 17.

On the other hand, in the receiver 4, the reception unit 22 receives the signal transmitted from the transmitter 6, through the antenna 21, and the received signal is demodulated by the demodulation unit 23. The demodulates signal contains the tone signal of 320 Hz. Therefore, the signal is extracted by the BPF 26, and rectified and detected in the rectifying detector 27. In the comparator 28, the output signal of the rectifying detector 27 is compared with the preset threshold. When the comparator 28 judges that the output signal exceeds the preset threshold, the comparator outputs a switch signal for opening the pair of the switchover portions 29a and 29b of the switch 29.

In this structure, when radio wave from the sensor device 1 doesn't reach to the receiver 4, the tone signal transmitted from the sensor device 1 during the detection of electrode detachment state by the electrode detachment detection unit 12 cannot be detected by the bandpass filter 26 in the receiver 4. To solve this problem, there may provided, in the FIG. 16, control circuit composed of D-type flip-flop 293, AND circuit 292 and OR circuit, to which outputs of comparator 28 and the radio wave level detection unit 22a are connected. The control circuit 29 actualizes the maintain the signal state of output of the comparator 28 right before the radio wave out-of-reach state is detected, by inputting the output of the radio wave level detection unit 22a into D-type flip-flop 293, although the transmitted tone signal cannot be detected by bandpass filter 26. In case when the radio wave from the sensor device 1 reaches to the receiver 4 and the tone signal which is generated by the electrode detachment detection unit 12 in the sensor device 1 is detected by bandpass filter 26 in the receiver 4, since output of comparator 28 is High Level, output of OR circuit is also High Level and switch 29a is open-state. After that, the radio wave from the sensor device 1 doesn't reach to the receiver 4 and the tone signal generated by the electrode detachment detection unit 12 in the sensor device 1 hasn't come to be detected by bandpass filter 26 in the receiver 4, output of the comparator 28 changes to Low Level from High Level, and has been transmitted to D-type flip-flop 293 and OR circuit 291. Simultaneously, output of the radio wave level detection unit 22a become High Level from Low Level and has been transmitted to D-type flip-flop 293 and AND circuit 292. As the result, output of D-type flip-flop 293 is inverted from Low Level to High Level, output of AND circuit 292 becomes High Level, and hence, output of OR circuit 291 become High Level and switch 29a maintains the open-state. Therefore, the connection unit 30 enters a state a where the connection with the amplitude adjusting unit 25 is interrupted. As seen from the display device 3 connected to the connection unit 30, this state is identical with that in the case where the display device is directly connected through a cord to the electrodes attached to the patient and one or both of the electrodes is detached from the patient. The display device 3 continues to detect and display the electrode detachment since the open-state of switch 29a right before detection of the radio wave out-of-reach state is maintained even though the radio wave out-of-reach state abruptly happens.

When the electrode(s) which has been once detached is again attached, the electrode detachment detection unit 12 stops the transmission of the control signal. Consequently, the tone oscillation unit 13 ceases the transmission of the tone signal, so that the output of the adding circuit 14 contains only the output signal of the AC amplification unit 11. In the receiver 4, therefore, the BPF 26 produces no output, so that the comparator 28 does not transmit the switch signal. The switchover portions 29a and 29b of the switch 29 are close, and the output of the amplitude adjusting unit 25 reaches the connection unit 30. As a result, the display device 3 again displays the electrocardiographic signal.

Next, it is assumed that the patient returns to the bedside and the electrocardiographic signal is to be monitored on the display device 7 serving as a bedside monitor. At this time, the receiver 4 is dismounted from the display device 3, and the connector 5a of the receiver is joined to the connector 8 of the display device 7. Also in this case, in the same manner as the display device 3, the process is performed in the same manner as the case where a signal obtained from an electrode provided with a cord is processed.

In order to enhance the convenience of the receiver, a simple indicator may be added to the receiver.

For example, a battery exhaustion detection unit 31a which detects voltage reduction of the power source unit (battery) 31 of the receiver 4 is additionally provided so as to inform the user of the voltage reduction by means of an alarm 100c.

When the reception unit 22 cannot detect the radio wave transmitted from the sensor device 1, a radio wave level detection unit 22a detects this state, and informs the user of the state by means of an alarm 100a.

A battery exhaustion detection unit 12a which detects voltage reduction of the power source unit (battery) 18 of the transmitter 6 is additionally provided. When the voltage reduction is detected, a tone oscillation unit 13a generates a tone signal. The tone signal is added to the electrocardiographic signal in the adding circuit 14, and then transmitted in the form of a radio wave together with the electrocardiographic signal through the modulation unit 15 and the transmission unit 16. The tone signal is then detected by a BPF 26a of the receiver 4, and sensed through a rectifying detector 27a and a comparator 28a. The voltage reduction is then informed to the user by means of an alarm 100b.

When the electrode detachment signal is detected by the electrode detachment detection unit 12 of the transmitter 6, the tone oscillation unit 13 generates a tone signal. The tone signal is added to the electrocardiographic signal in the adding circuit 14, and then transmitted in the form of a radio wave together with the electrocardiographic signal through the modulation unit 15 and the transmission unit 16. The tone signal is then detected by the BPF 26 of the receiver 4, and sensed through the rectifying detector 27 and the comparator 28. The switch 29 is turned off, and at the same time the voltage reduction is informed to the user by means of an alarm 100d.

Figure 15:
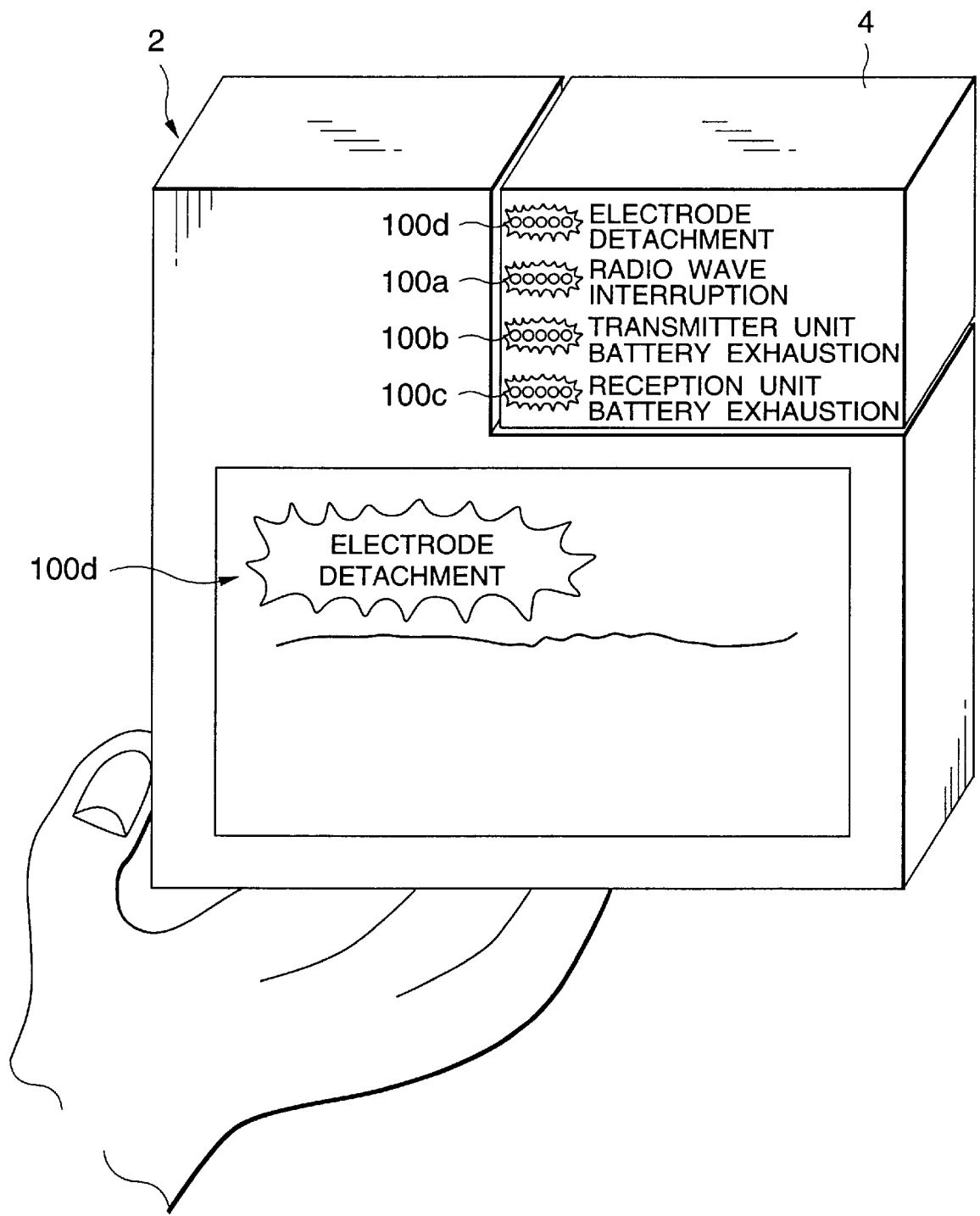
FIG. 15 is a view showing the receiver containing alarm means.

The alarming may be conducted by one of a method (FIG. 15) in which LEDs or a liquid crystal display device is used for visually indicating such an abnormal condition, and that in which a buzzer is used for acoustically indicating such an abnormal condition.

The receiver 4 is sequentially connected to biomedical signal input portions of various other devices, and is not fixed to a given position. Therefore, it is required to ensure a sensitivity at which reception is enabled under any condition. In order to perform reception more surely, the receiver is provided with a function of polarization diversity, so that stable reception is ensured even when the receiver is connected to various kinds of other devices.

Figure 12:
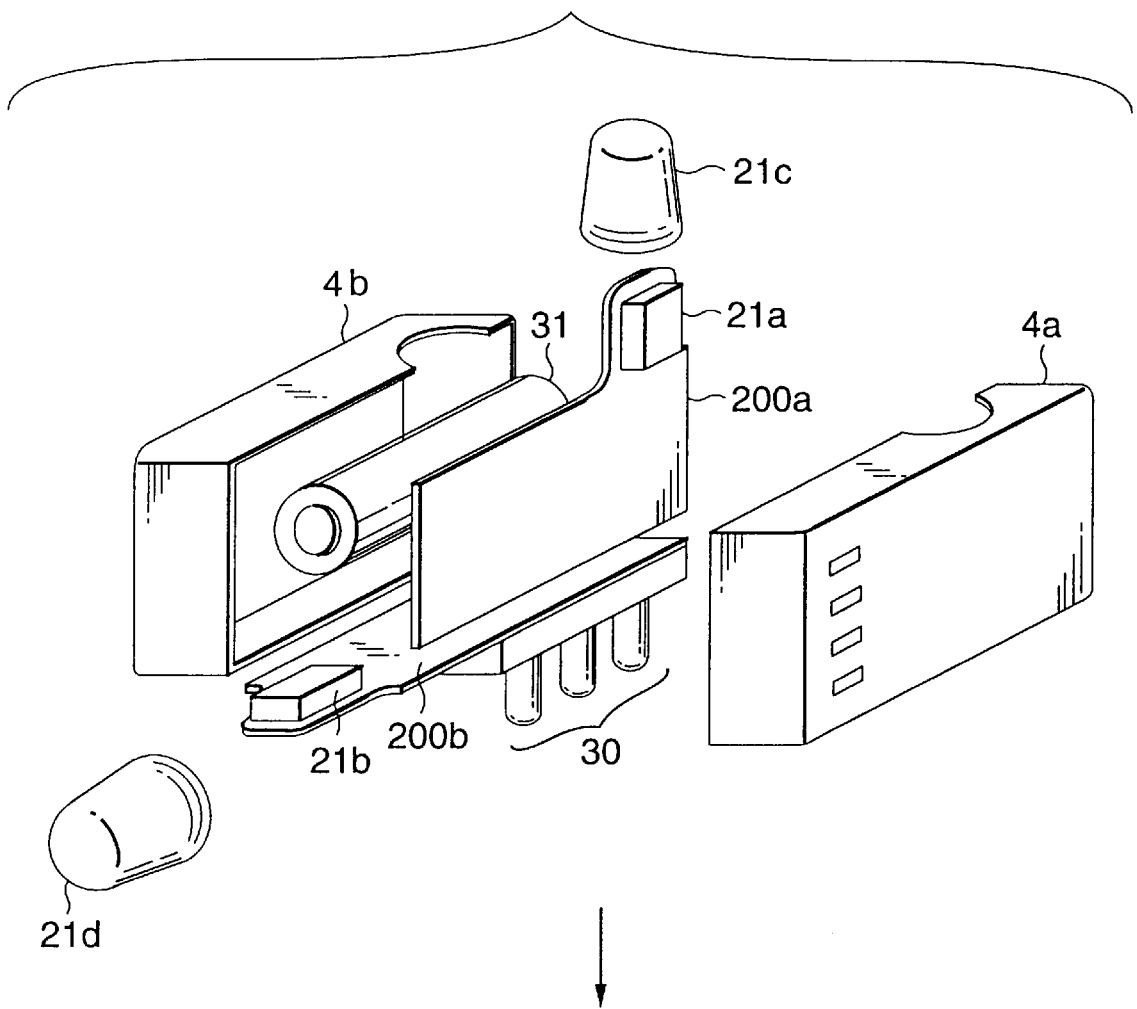
FIG. 12 is an exploded view of a receiver of the present invention.
Figure 13:
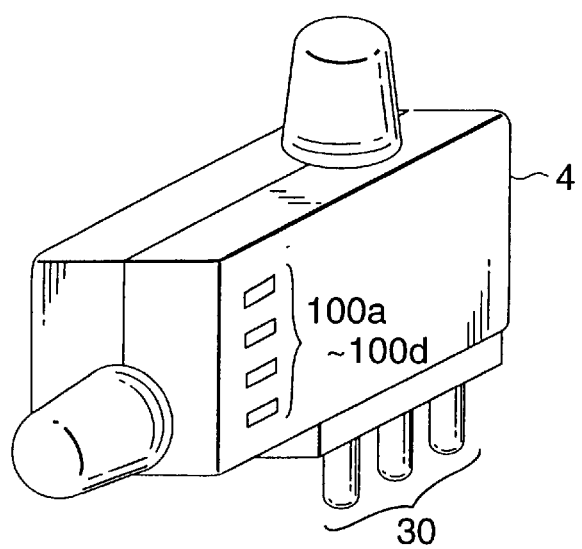
FIG. 13 is an schematic view of the receiver of the present invention.
Figure 14:
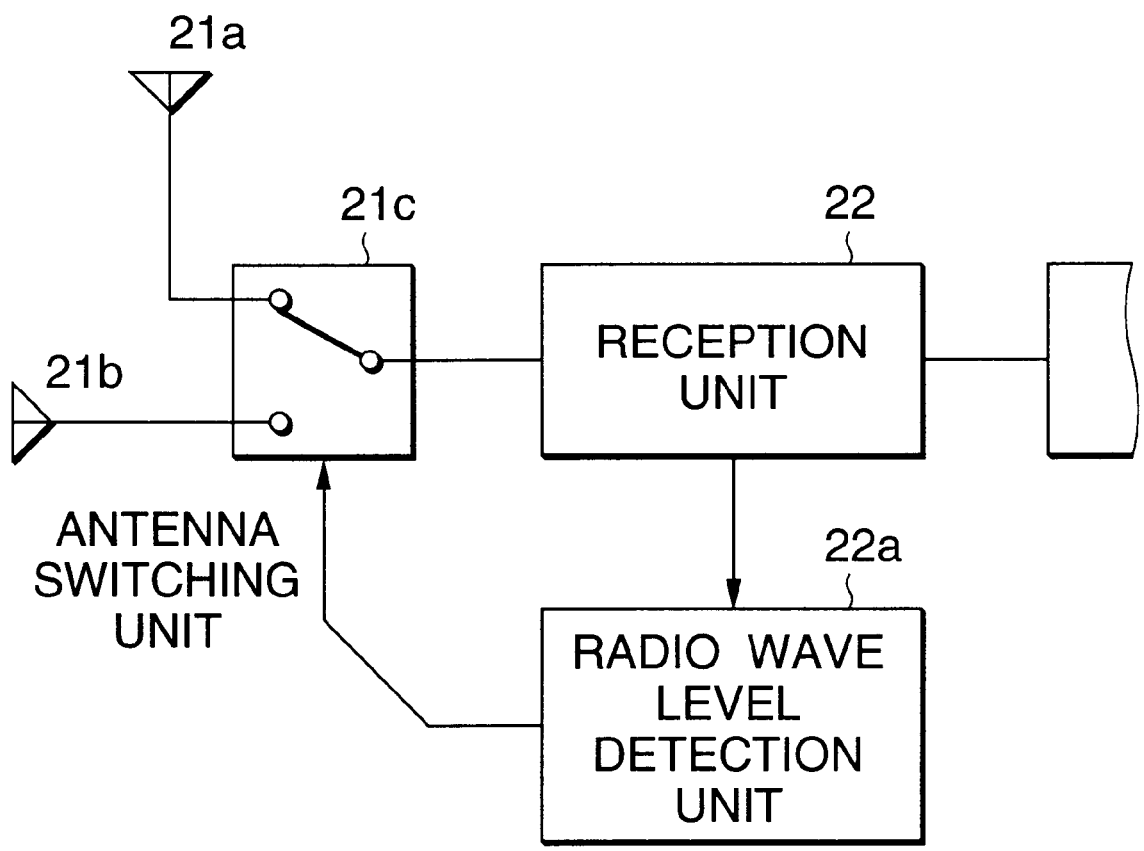
FIG. 14 is a diagram showing the configuration of the receiver of the present invention.

FIG. 12 is an exploded view of the receiver 4, and FIG. 13 is an external view of the receiver. In the receiver, small chip dielectric antennas 21a and 21b are respectively projectingly mounted on the upper side faces of the case in different directions, for examples, directions which are perpendicular to each other, so that the ground direction of a circuit board 200a in the vicinity of the chip dielectric antenna 21a is perpendicular to that of a circuit board 200b in the vicinity of the chip dielectric antenna 21b, thereby compensating their directivities.

The small ship dielectric antennas 21a and 21b have a size which is about some tenths of the wavelength of the transmitted signal and which is substantially smaller than a monopole antenna (one fourth of the wavelength). The projecting portions of the antennas 21a and 21b are protected by caps of several millimeters to several centimeters, and hence the convenience is not impaired.

Figure 10:
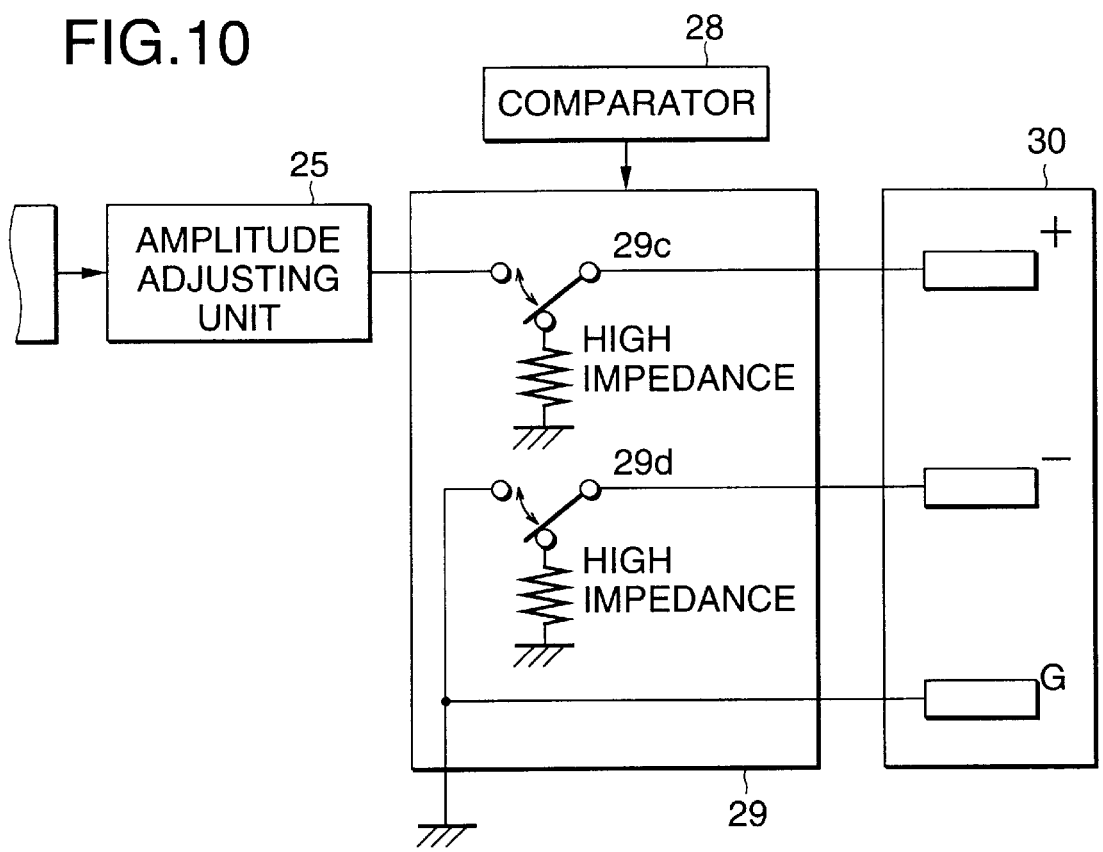
FIG. 10 is a diagram showing the configuration of an example of the switch used in the present invention.
Figure 11:
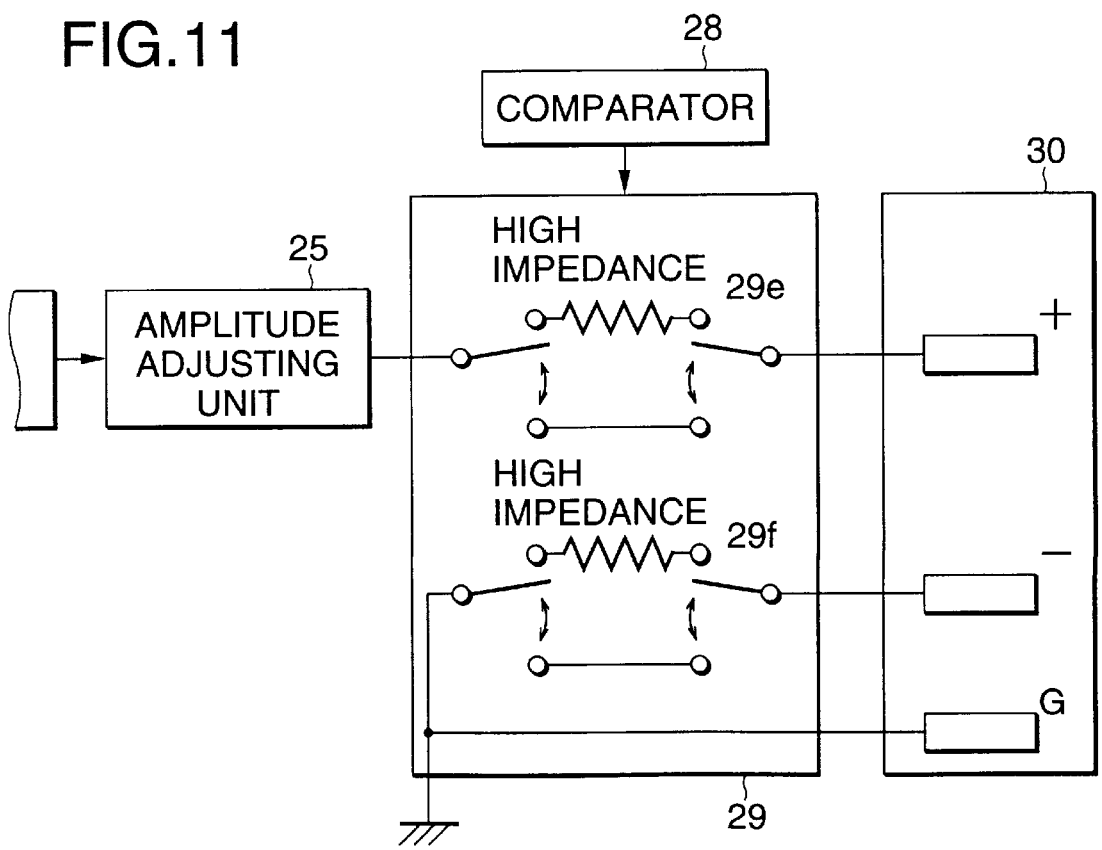
FIG. 11 is a diagram showing the configuration of another example of the switch used in the present invention.

On the circuit boards 200a and 200b, disposed are the components constituting the receiver 4 and having the functions shown in the block diagram of FIG. 1, including the reception unit 22, the demodulations unit 23, the BPF 24, the BPF 26, the rectifying detector 27, the comparator 28, the amplitude adjusting unit 25, the switch 29, the radio wave level detection unit 22a, the BPF 26a, the rectifying detector 27a, the comparator 28a, and the battery exhaustion detection unit 31a.

the switch 29 may be formed by switches 29c and 29d shown in FIG. 10, or may be configured so as to produce a high-impedance state as seen from the connection unit 30. Alternatively, the switch 29 may be formed by switches 29e and 29f which are used for switching over resistors between the amplitude adjusting unit 25 and the connection unit 30 as shown in FIG. 11. Any kind of a switchover method may be used as far as it is possible to produce a state in which the impedance as seen from the connection unit 30 is made higher.

Figure 5:
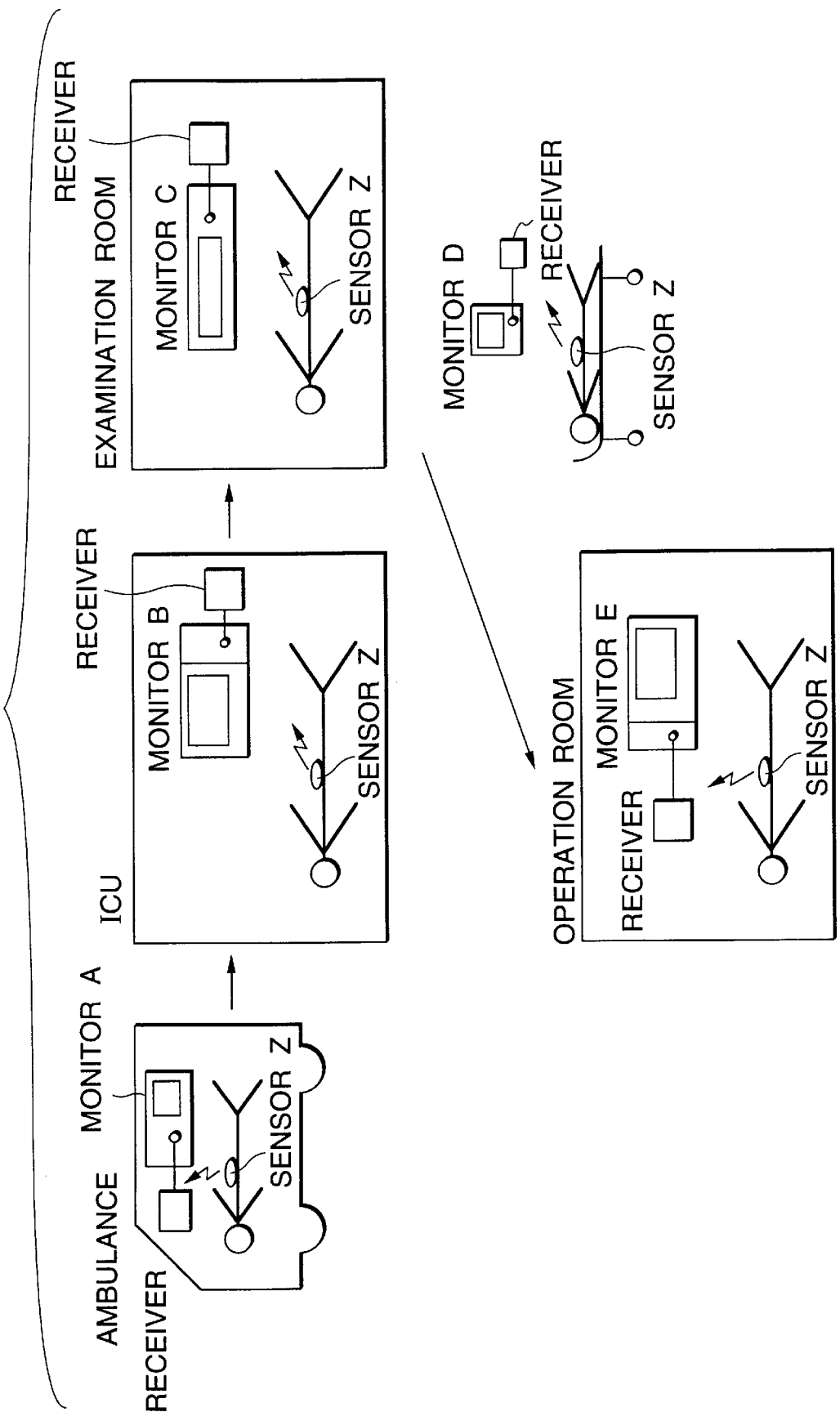
FIG. 5 is a diagram illustrating the state where the sensor device and the receiver shown in FIG. 1 are used in different locations.

An example in which the present system is used in an emergency rescue scene will be described with reference to FIG. 5. As shown in the figure, the sensor device 1 (sensor Z) is attached to a patient and the patient is then lifted in an ambulance car. The receiver 4 is mounted on a monitor device A in the ambulance car, so that an electrocardiograph is displayed on the monitor device A. When the ambulance car arrives at a hospital, the receiver 4 is dismounted from the monitor device A, and then mounted on a monitor device B in an ICU, so that an electrocardiograph is displayed on the monitor device B. Next, the receiver 4 is dismounted from the monitor device B, and the patient is then moved into an examination room. The receiver 4 is mounted on a monitor device C in the room, so that an electrocardiograph is displayed on the monitor device C. Thereafter, the receiver 4 is dismounted from the monitor device C, and then mounted on a monitor device D. The patient is then transported while an electrocardiograph is displayed on the monitor device D. When the patient arrives at an operation room, the receiver 4 is dismounted from the monitor device D, and then mounted on a monitor device E in the operation room, so that an electrocardiograph is displayed on the monitor device E. In this way, even when the monitor device is replaced with a new monitor device disposed in the destination place of each movement of the patient, an electrocardiograph can be displayed on the new monitor device, while the sensor device 1 which has been once attached to the patient is never required to be detached from the patient and no burden is imposed on the patient. Instead, in a case when other receiver corresponding to carrier-frequency of the sensor device 1 is connected to monitor in hospital in advance, medical staff doesn't need to remove nor reinsert the receiver 5.

Figure 6:
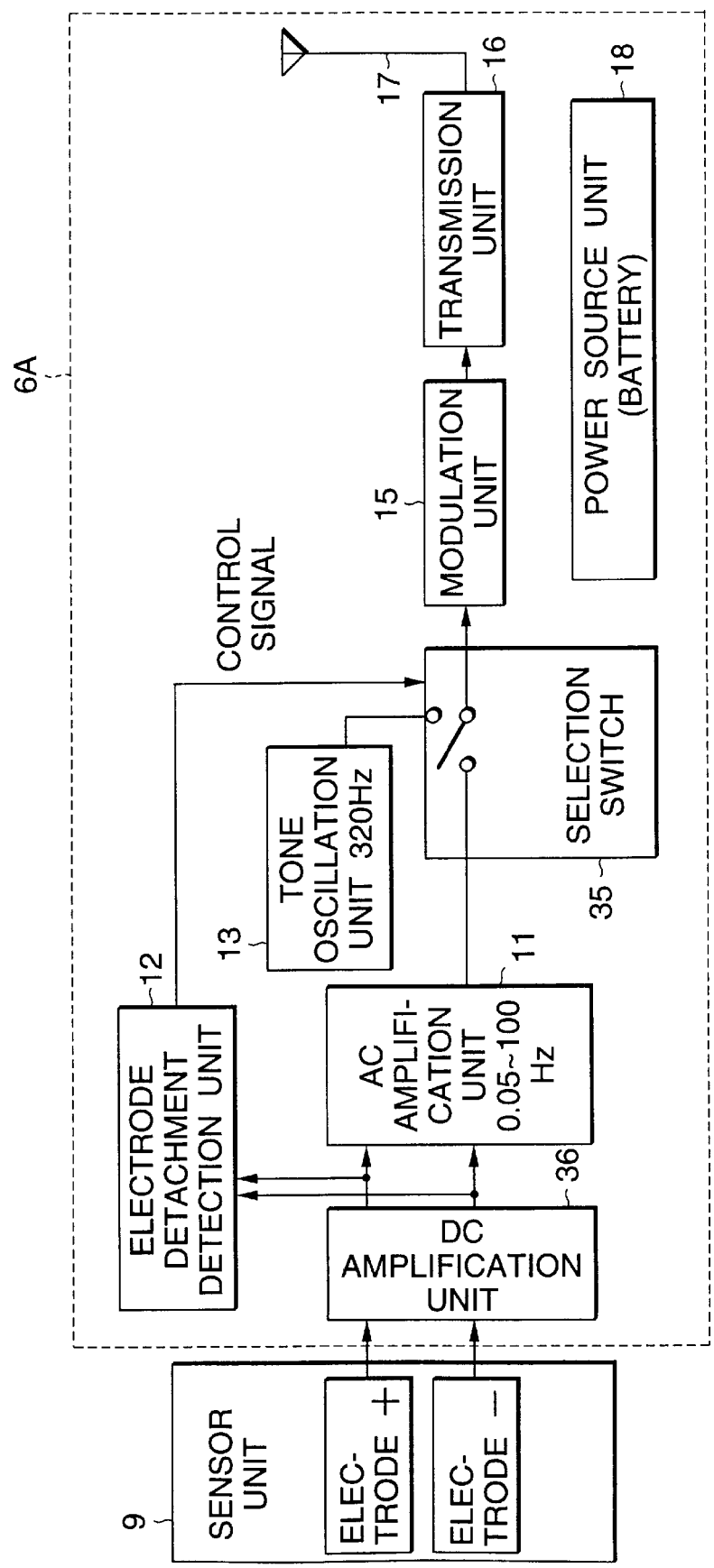
FIG. 6 is a diagram showing the configuration of the sensor device of a second embodiment of the invention.

Next, a second embodiment will be described. The embodiment is different from the first embodiment in configuration of the transmitter, or has a transmitter 6A shown in FIG. 6. The transmitter is configured in the following manner. In place of the adding circuit 14 of the first embodiment, a selection switch 35 is disposed. Normally, the AC amplification unit 11 is connected to the modulation unit 15. When the electrode detachment detection unit 12 detects electrode detachment and outputs the control signal, the connection between the AC amplification unit 11 and the modulation unit 15 is interrupted, and the tone oscillation unit 13 is connected to the modulation unit 15. The AC amplification unit 11, the selection switch 35, the modulation unit 15, the transmission unit 16, and the antenna 17 constitute the transmitting means. The other components are configured in the same manner as those of the first embodiment. Means for generating kinds of alarm is just omitted but applicable (Other embodiments is the same way.). Also this configuration can attain the same function and effect as those of the first embodiment.

Figure 7:
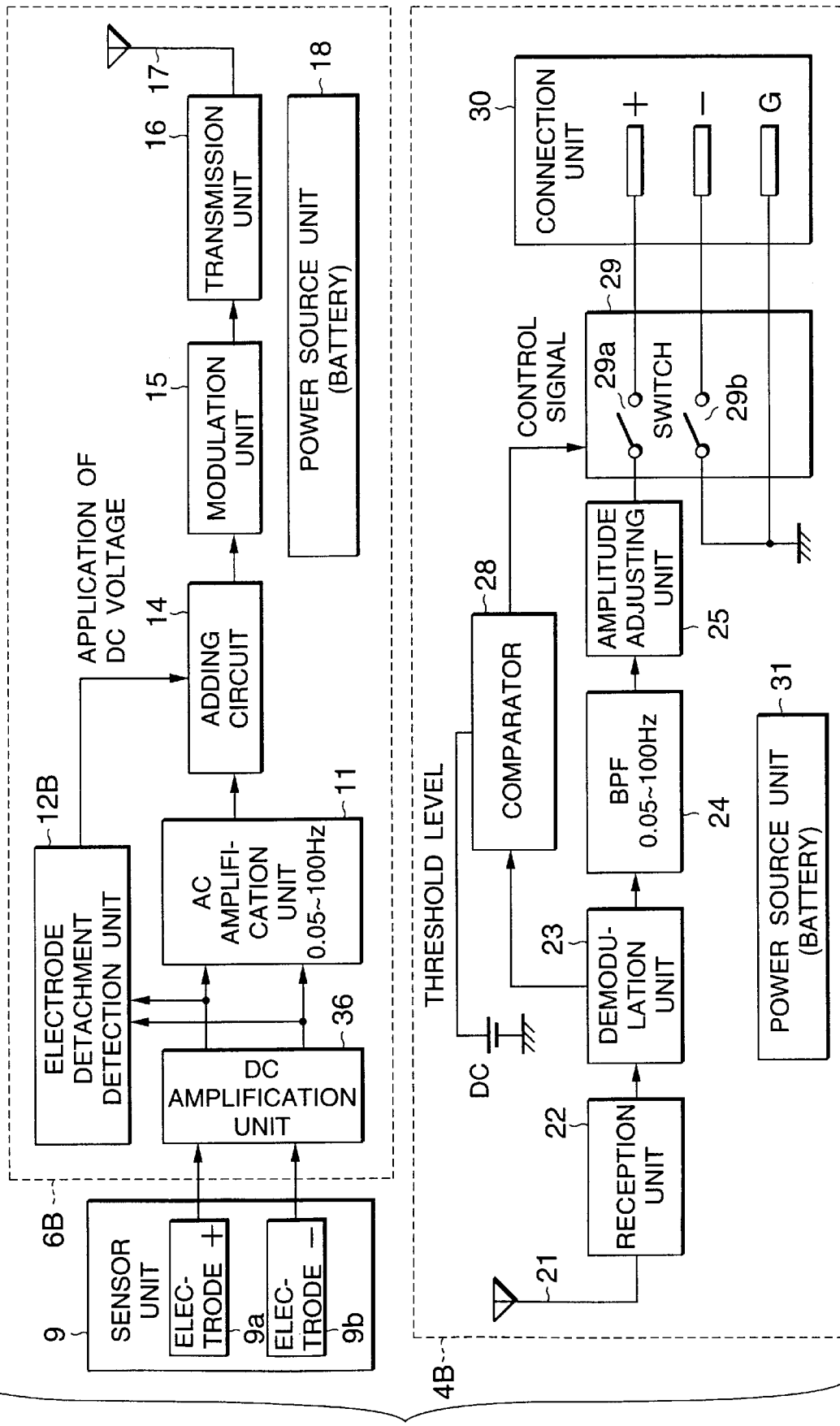
FIG. 7 is a diagram showing the configuration of the sensor device and the receiver of a third embodiment of the invention.

Next, a third embodiment will be described. The embodiment is different from the first embodiment in configuration of the transmitter and the receiver, or has a transmitter 6B and a receiver 4B shown in FIG. 7. In the transmitter 6B, the tone oscillation unit 13 of the first embodiment is not disposed, and, when an electrode detachment detection unit 12B detects electrode detachment, a predetermined DC voltage is applied to the adding circuit 14. The electrode detachment detection unit 12B detects electrode detachment on the basis of the output signal of the sensor unit 9 which is amplified in the DC amplification unit 36.

In the embodiment, the electrode detachment detection unit 12B constitutes the first detecting means, and the DC amplification unit 36, the AC amplification unit 11, the adding circuit 14, the modulation unit 15, the transmission unit 16, and the antenna 17 constitute the transmitting means.

On the other hand, in the receiver 4B, the BPF 26 and the rectifying detector 27 of the first embodiment are not disposed, and the comparator 28 directly receives the output signal of the demodulation unit 23 and compares the signal with a preset threshold (a value which is lower than the voltage applied from the electrode detachment detection unit 12B to the adding circuit 14). In accordance with a result of the comparison, the switchover portions 29a and 29b of the switch 29 is turned on or off in the same manner as the first embodiment. The comparator 28 and switch 29 constitute the second detecting means. The other components are configured in the same manner as those of the first embodiment. The embodiment can attain an effect that the whole configuration can be simplified, and also the same function and effect as those of the first embodiment.

Figure 8:
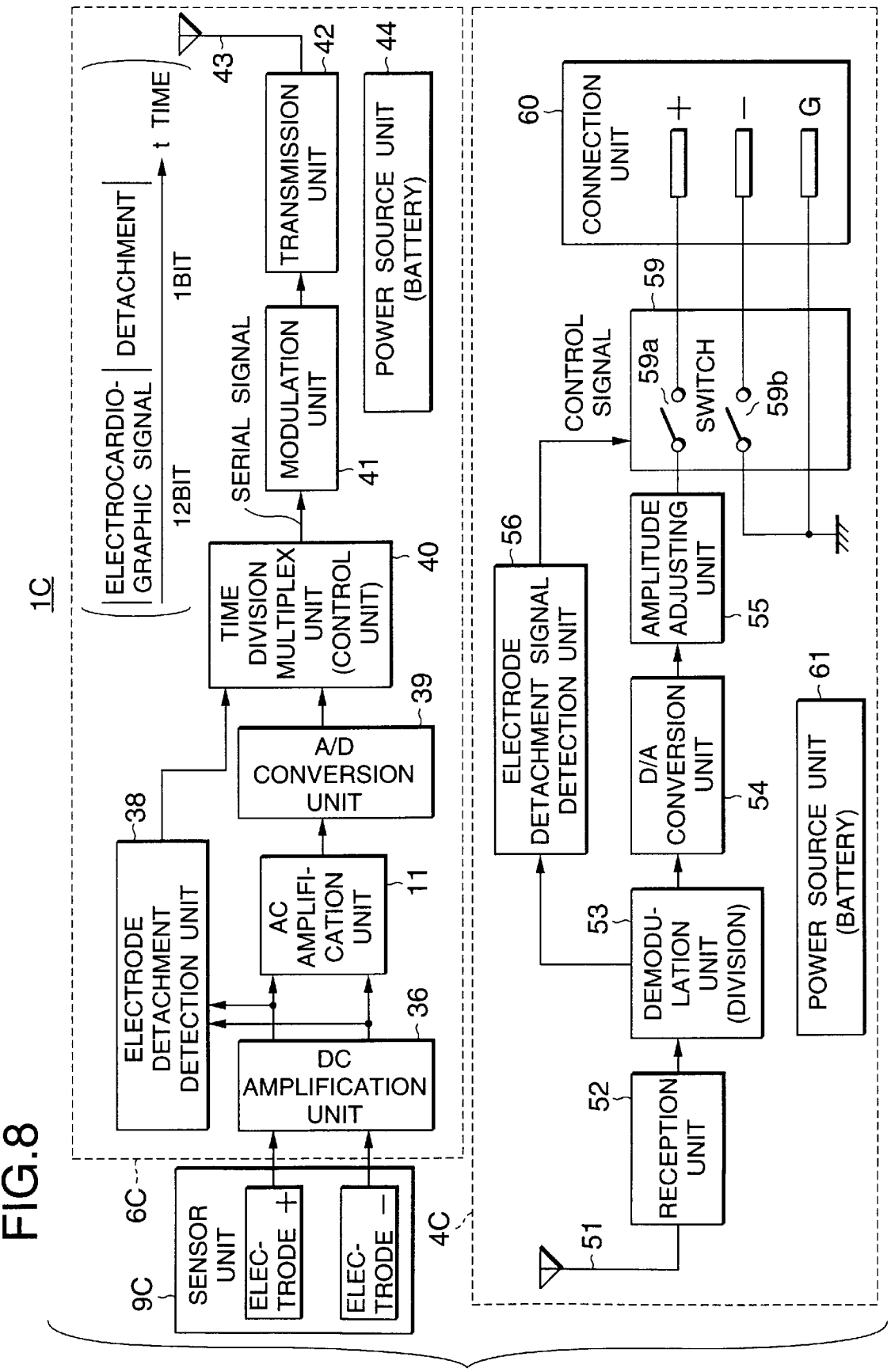
FIG. 8 is a diagram showing the configuration of the sensor device and the receiver of a fourth embodiment of the invention.
Figure 9:
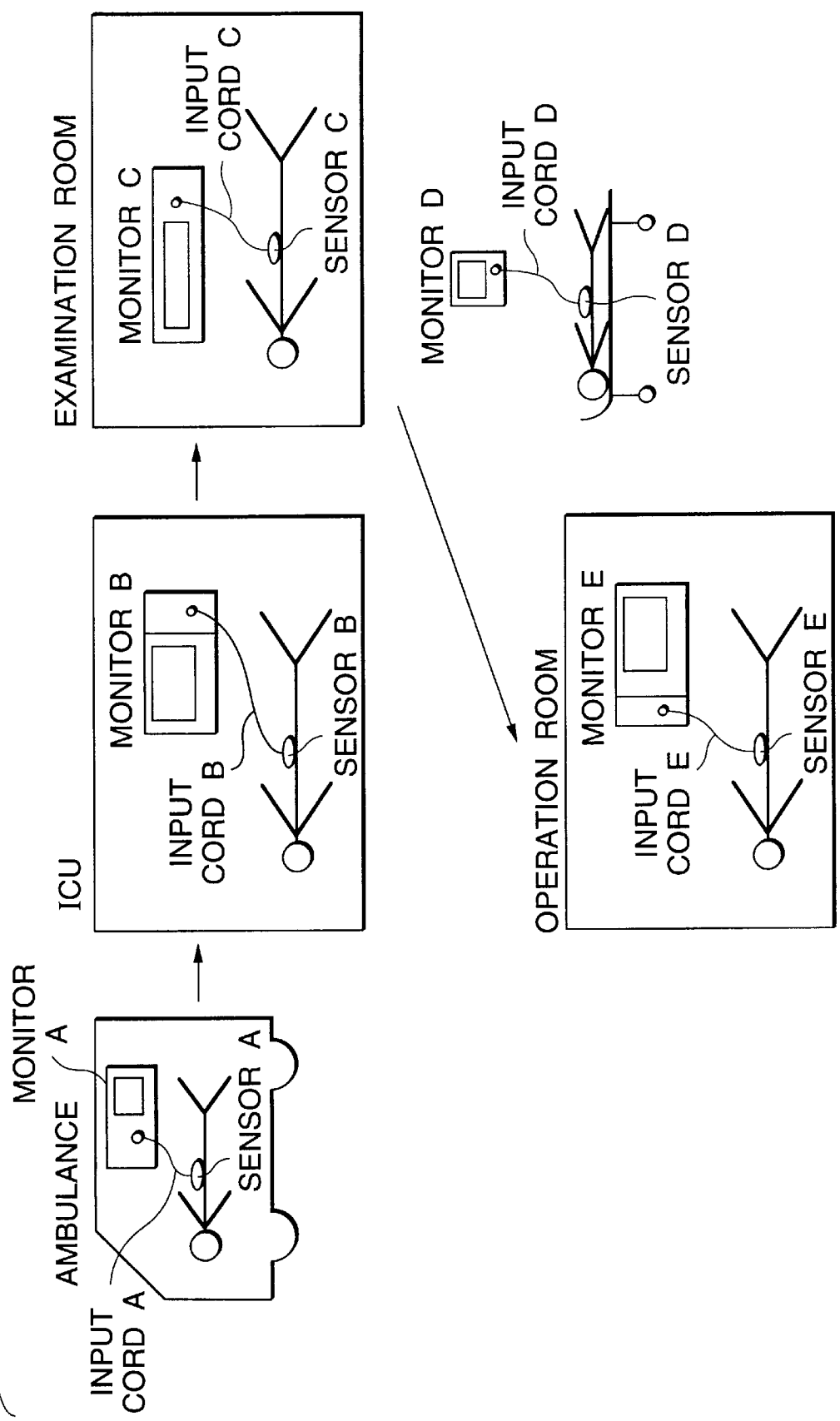
FIG. 9 is a diagram illustrating the connecting state between a sensor device and a monitor device in the prior art, in different locations.

Next, a fourth embodiment will be described. In the embodiment, the detected electrocardiographic signal is processed after digitization. FIG. 8 shows the configuration of a sensor device 1C and a receiver 4C of the embodiment. As shown in the figure, the sensor device 1C consists of a sensor unit 9C and a transmitter 6C. The sensor unit 9C is configured in the same manner as the sensor unit of the above-described embodiments. The transmitter 6C consists of: a DC amplification unit 36 and an AC amplification unit 11 which amplify the output signal of the sensor unit 9C; an electrode detachment detection unit 38 which detects electrode detachment on the basis of an output signal of the DC amplification unit 36 and outputs a digital signal indicative of the detachment; and A/D conversion unit 39 which digitizes the output signal of the AC amplification unit 11; a time division multiplex unit 40 which time division multiplexes signals supplied from the electrode detachment detection unit 38 and the A/D conversion unit 39; a modulation unit 41 which modulates the carrier wave signal by an output signal of the time division multiplex unit 40; a transmission unit 42 and an antenna 43 which cooperate to transmit an output signal of the modulation unit 41, in the form of a radio signal to the outside; and a power source unit 44 which supplies a required power to the components.

In the embodiment, the electrode detachment detection unit 38 constitutes the first detecting means, and the AC amplification unit 11, the time division multiplex unit 40, the modulation unit 41, the transmission unit 42, and the antenna 43 constitute the transmitting means.

On the other hand, the receiver 4C consists of: an antenna 51; a reception unit 52 which receives the radio signal through the antenna 51; a demodulation unit 53 which demodulates the signal received by the reception unit 52; a D/A conversion unit 54 which converts an electrocardiographic signal output from the demodulation unit 53 into an analog signal; an emplitude adjusting unit 55 which attenuates or amplifies an output signal of the D/A conversion unit 54; an electrode detachment signal detection unit 56 which detects an electrode detachment signal from the signal demodulated by the demodulation unit 53; a switch 59 having a pair of switchover portions 59a and 59b which are simultaneously switched over in response to a control signal that is output when the electrode detachment signal detection unit 56 detects the electrode detachment signal; a connection unit 60 which is connected to one terminal of each of the switchover portions 59a and 59b of the switch 59, and also to an input portion of another device; and a power source unit 61. The power source unit 61 is a battery which supplies a required power to the above-mentioned components.

The output signal of the amplitude adjusting unit 55 is supplied to the other terminal of the switchover portion 59a of the switch 59. The connection unit 60 has a connector consisting of three pins in the same manner as the corresponding units of the above-described embodiments. Among the pins, a plus pin is connected to the one terminal of the switchover portion 59a of the switch 59, a minus pin is connected to the one terminal of the switchover portion 59b of the switch 59, and a ground pin is connected to the other terminal of the switchover portion 59b of the switch 59. When the control signal of the electrode detachment signal detection unit 56 is not output, the pair of switchover portions 59a and 59b of the switch 59 are normally closed.

In the embodiment, the antenna 51, the reception unit 52, the demodulation unit 53, and the D/A conversion unit 54 constitute the receiving means, the electrode detachment signal detection unit 56 and switch 59 constitute the second detecting means, the amplitude adjusting unit 55 constitutes the amplitude adjusting means, and the connection unit 60 constitutes the connecting means.

According to this configuration, the same function and effect as those of the above-described embodiments can be attained. Furthermore 6C and the receiver 4C are performed in the form of a digital signal, and hence the electrocardiographic signal is hardly affected by noises so that the electrocardiographic signal can be monitored more correctly.

The alarm method and the variable impedance means which are described in the first embodiment may be applied to the other embodiments. The radio wave transmitted from the sensor device is set to have a frequency at which radio interference with other sensor devices can be avoided. In order to enable the user to easily visually recognize a pair of a sensor device and a receiver, pairs of a sensor device and a receiver may be provided with cases of different colors or pasted with seals of different colors, respectively. The components of the sensor unit of the sensor device are not restricted to electrodes, and the sensor unit may be configured by other members which can detect a biomedical signal of another kind from a subject.

In the system of the present invention, signal transmission and reception between the sensor device and the other device which processes a biomedical signal detected by the sensor device is performed in the form of a radio signal, and hence the biomedical signal can be supplied to the other device by only connecting the receiver to the biomedical signal input portion of the other device. Even when the device which processes a biomedical signal from the sensor device is replaced with a new device, therefore, the biomedical signal can be rapidly supplied to the new device by a simple operation while the sensor device remains to be attached to the patient and no burden is applied to the patient. In the system, when an electrode of the sensor device is detached, the receiver causes the detachment state to be artificially produced in the biomedical signal input portion of the other device. If the device has functions of detecting electrode detachment based on a signal from the input portion and performing a process in accordance with the detachment, therefore, the device can sufficiently exhibit the functions.

In the sensor device of the present invention, a biomedical signal is transmitted in the form of a radio signal, and, when an electrode attached to a living body is detached from the living body, a signal indicative of the detachment can be transmitted in the form of a radio wave.

In the receiver of the present invention, a biomedical signal in the received signal is attenuated or amplified so as to have the same level as a signal supplied from a biomedical electrode through a wire, and then supplied to the biomedical signal input portion of the other device. In the receiver, when the electrode detachment signal is detected, the connection between the amplitude adjusting means and the connecting means is interrupted in response to the detection. In the other device which is connected to the receiver, therefore, the input potential of the biomedical signal input portion is in a floating state.

What is claimed is:

1. A medical telemetry system comprising:
a sensor device comprising;
a sensor unit detecting a biomedical signal;
first detecting means for detecting a state of said sensor unit in which said sensor unit cannot detect the biomedical signal, and for outputting an undetectable state signal indicative of the state; and
transmitting means for transmitting the undetectable state signal and the biomedical signal in the form of a radio signal;
a receiver adapted to be interchangeable connected to a plurality of various monitoring devices, said receiver comprising;
receiving means for receiving the radio signal transmitted from said sensor device;
second detecting means for detecting the undetectable state signal, and for outputting an alarm signal when the undetectable state signal is detected; and
connecting means for supplying the biomedical signal of the received radio signal and the alarm signal to a signal input portion of one of said plurality of various monitoring devices;
wherein said second detecting means comprises a variable impedance switching device for varying an impedance to an output of said connecting means when the undetectable state signal is detected.

2. A receiver for receiving a radio signal containing a biomedical signal detected by a sensor, and an undetectable state signal indicative of an undetectable state of said sensor, said receiver adapted to be interchangeably connected to a plurality of various monitoring devices, said receiver comprising:

receiving means for receiving the radio signal;

detecting means for detecting the undetectable state signal; and connecting means for outputting the biomedical signal of the received radio signal and the undetectable state signal of the detecting means to an input portion of one of said plurality of various monitoring devices;

wherein said detecting means comprises a variable impedance switching device for varying an impedance to an output of said connecting means when the undetectable state signal is detected.

3. A method of using a medical telemetry system having a sensor device comprising a sensor unit for detecting a biomedical signal of a patient, and transmitting means for transmitting the biomedical signal from said sensor device, in the form of a radio signal, and a receiver comprising receiving means for receiving the radio signal transmitted form said sensor device and connecting means for outputting the received biomedical signal to an input portion of one of a plurality of devices, comprising the steps of:

maintaining a state where said sensor device is enabled to detect the biomedical signal during movement of the patient to a different place for a next stage treatment; and changing a connection of said connecting means to output the received biomedical signal to a different one of said plurality of devices when the patient arrives at the different place for the next stage treatment.

4. The method of using a medical telemetry system according to claim 3, wherein said maintaining state step is carried out at a rescue stage of the patient, and said changing connection step is carried out when the patient is moved to a hospital.

5. The method of using a medical telemetry system according to claim 4, further comprising the steps of:

maintaining a state where said sensor device is enabled to detect the biological signal when the patient is moved from a first room to a second room in the hospital; and changing the connection of said connecting means to output the received biological signal to a different one of said plurality of devices when patient arrives at said second room.

6. A medical telemetry system comprising:

a sensor device comprising;

an electrode adapted to be attached to a living body, said electrode outputting a biomedical signal of said living body;

first detecting means for detecting an electrode detachment from said living body, and for outputting an electrode detachment signal indicative of the electrode detachment;

transmitting means for transmitting the electrode detachment signal form said first detecting means and the biomedical signal from said electrode, in the form of a radio signal;

a receiver adapted to be connected to a biomedical signal input portion of a device comprising:

receiving means for receiving the radio signal transmitted from said sensor device;

amplitude adjusting means for attenuating or amplifying the biomedical signal of the radio signal received by said receiving means, said amplitude adjusting means outputting an adjusted biomedical signal;

connecting means for supplying said adjusted biomedical signal to said biomedical signal input portion; and second detecting means for detecting the electrode detachment signal of the radio signal received by said receiving means and for interrupting a connection between said amplitude adjusting means and said connecting means when said second detecting means detects the electrode detachment signal.

7. The medical telemetry system according to claim 6, wherein said second detecting means interrupts said connection between said amplitude adjusting means and said connecting means by increasing an impedance of the connection, when said second detecting means detects the electrode detachment signal.

8. A receiver for a medical telemetry system and adapted to be connected to a biomedical signal input portion of a device, the receiver comprising:

receiving means for receiving a radio signal containing a biomedical signal and an electrode detachment signal indicative of electrode detachment;

amplitude adjusting means for attenuating or amplifying the biomedical signal of said radio signal received by said receiving means, said amplitude adjusting means outputting an adjusted biomedical signal;

connecting means for supplying said adjusted biomedical signal to said biomedical signal input portion;

first detecting means for detecting the electrode detachment signal of said radio signal received by said receiving means; and for inhibiting a connection between said amplitude adjusting means and said connecting means when said second detecting means detects the electrode detachment signal.

9. The receiver for a medical telemetry system according to claim 8, wherein the second detecting means inhibits the connection between the amplitude adjusting means and the connecting means by increasing an impedance of the connection when the electrode detachment signal is detected.

10. A medical telemetry system comprising:

a sensor device comprising;

a sensor unit detecting a biomedical signal;

first detecting means for detecting a state of said sensor unit in which said sensor unit cannot detect the biomedical signal, and for outputting an undetectable state signal indicative of the state; and transmitting means for transmitting the undetectable state signal and the biomedical signal in the form of a radio signal;

a receiver adapted to be interchangeably connected to a plurality of various monitoring devices, said receiver comprising;

receiving means for receiving the radio signal transmitted from said sensor device;

second detecting means for detecting the undetectable state signal, and for outputting an alarm signal when the undetectable state signal is detected; and connecting means for supplying the biomedical signal of the received radio signal and the alarm signal to a signal input portion of one of said plurality of various monitoring devices;

wherein said receiver further comprises:

radio wave level detection means for detecting a radio wave level of the radio signal from said transmitting means, and for determining a radio wave out-of-reach state based upon the level of radio wave detected; and control means for maintaining said alarm signal until the radio wave out-of-reach state is determined.

11. A medical telemetry system comprising:
a sensor device comprising;
  a sensor unit which detects and outputs a biomedical signal;
  first detecting means for detecting a state of said sensor unit in which said sensor unit cannot detect the biomedical signal, and for outputting an undetectable state signal indicative of the state; and
  transmitting means for transmitting said undetectable state signal from said first detecting means and said biomedical signal from said sensor unit, in the form of a radio signal;
a receiver comprising;
a receiver means for receiving said radio signal transmitted from said sensor device;
radio wave level detection means for detecting a radio wave level of said radio signal, said radio signal wave level detection means for determining a radio wave out-of-reach state;
second detecting means for detecting said undetectable state signal of the radio signal received by said receiving means;
control means for maintaining said undetectable state signal until the radio wave out-of-reach state is determined.

12. A receiver for receiving a radio signal containing a biomedical signal detected by a sensor, and an undetectable state signal indicative of an undetectable state of said sensor, said receiver adapted to be interchangeably connected to a plurality of various monitoring devices, said receiver comprising;
  receiving means for receiving the radio signal;
  detecting means for detecting the undetectable state signal;
  connecting means for outputting the biomedical signal of the received radio signal and the undetectable state signal of the detecting means to an input portion of one of said plurality of various monitoring devices;
  radio wave level detection means for detecting a radio wave level of the radio signal and for determining a radio wave out-of-reach state;
  control means for maintaining said undetectable state signal until the radio wave out-of-reach state is determined.

13. The receiver according the claim 12, further comprising, amplitude adjusting means for adjusting an amplitude of the biomedical signal of the received radio signal to a same level as the biomedical signal detected by said sensor, and said amplitude adjusting means outputting an adjusted biomedical signal to said connecting means.

14. A medical telemetry system comprising:
a sensor device comprising,
  an electrode adapted to be attached to a living body, said electrode outputting a biomedical signal of said living body;
  first detecting means for detecting electrode detachment and for outputting an electrode detachment signal indicative of the electrode detachment; and
  transmitting means for transmitting the electrode detachment signal from said first detecting means and said biomedical signal from said electrode, in the form of a radio signal; and
a receiver adapted to be connected to a biomedical signal input portion of a device, the receiver comprising,
  receiving means for receiving said radio signal containing said biomedical signal and said electrode detachment signal indicative of electrode detachment;
  amplitude adjusting means for attenuating or amplifying the biomedical signal of said radio signal received by said receiving means, said amplitude adjusting means outputting an adjusted biomedical signal;
  connecting means for supplying said adjusted biomedical signal to said biomedical signal input portion; and
  second detecting means for detecting the electrode detachment signal of said radio signal received by said receiving means; and for inhibiting a connection between said amplitude adjusting means and said connecting means when said second detecting means detects the electrode detachment signal.

15. A method of using a medical telemetry system having a sensor device comprising a sensor unit for detecting a biomedical signal, and transmitting means for transmitting the biomedical signal from said sensor device, in the form of a radio, and a receiver comprising receiving means for receiving the radio signal transmitted from said sensor device and connecting means for the received biomedical signal to an input portion of one of a plurality of devices, comprising the steps of:
  maintaining a state where said sensor device is enabled to detect the biological signal during movement of the patient from a first room to a second room in the hospital; and
  changing a connection of said connecting means to output the received biological signal to a different one of said plurality of devices when patient arrives at said second room.

* * * * *